(12) United States Patent
Sundermeyer et al.

(10) Patent No.: US 6,482,381 B1
(45) Date of Patent: Nov. 19, 2002

(54) METHOD FOR HYDROGENATING HALOGEN-SUBSTITUTED SILICON COMPOUNDS

(75) Inventors: Wolfgang Sundermeyer, Neckargemünd (DE); Hans Liesenhoff, Neuhäusel (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/646,870

(22) PCT Filed: Mar. 2, 1999

(86) PCT No.: PCT/EP99/01352

§ 371 (c)(1),
(2), (4) Date: Sep. 25, 2000

(87) PCT Pub. No.: WO99/48812

PCT Pub. Date: Sep. 30, 1999

(30) Foreign Application Priority Data

Mar. 23, 1998 (DE) .......................................... 198 12 587

(51) Int. Cl.$^7$ .......................... C01B 33/04; C01B 33/08
(52) U.S. Cl. ........................ 423/347; 423/342; 556/474

(58) Field of Search ................................ 423/342, 347; 556/474; 205/372, 402, 404

(56) References Cited

U.S. PATENT DOCUMENTS

| 4,405,591 | A | * | 9/1983 | Grosbois et al. |
| 4,623,531 | A | * | 11/1986 | Porcham |
| 5,126,473 | A | * | 6/1992 | Klockner et al. |
| 5,455,367 | A | * | 10/1995 | Klein et al. |

* cited by examiner

*Primary Examiner*—Steven Bos
(74) *Attorney, Agent, or Firm*—Oblon, Spivak, McClelland, Maier & Neustadt, P.C.

(57) ABSTRACT

Halogen-substituted silicon compounds are hydrogenated by reaction with hydrogen in a chloroaluminate salt melt as a reaction medium containing a finely divided metal capable of forming interstitial hydrides which are suspended in the melt, the finely divided interstitial metal hydrides being formed in situ in the melt by reduction of a metal halide with an electropositive element as a halogen acceptor I selected from the group consisting of magnesium, calcium and aluminum.

16 Claims, No Drawings

METHOD FOR HYDROGENATING HALOGEN-SUBSTITUTED SILICON COMPOUNDS

The invention relates to a process for the direct hydrogenation of halogen-substituted silicon compounds. Hydrogen-substituted silicon compounds have achieved particular industrial importance. Thus, monosilane ($SiH_4$) is used for producing high-purity silicon for semiconductor technology and, like disilane ($Si_2H_6$), for the (epitaxial) deposition of thin layers in microelectronics in the production of chips and thin-film solar cells. Moreover, in the preparation of organofunctional (poly)siloxanes, hydrogen-substituted organochlorosilanes, for example $(CH_3)_2SiHCl$, $(CH_3)SiH_2Cl$, $(CH_3)SiHCl_2$, etc., which are obtained only in insignificant amounts or in amounts which do not correspond to the respective demand in the industrial Müller-Rochow direct synthesis, are key compounds for the known hydrosilylation reaction.

There has therefore been no lack of attempts to produce the various silanes on an industrial scale. Neither the acidolysis of silicides nor the reaction of silicon tetrachloride with lithium alanate in ether solution are suitable for producing silanes inexpensively and in the required purity. The catalytic disproportionation of trichlorosilane carried out on a relatively large scale forms not only one part of monosilane but also three parts of silicon tetrachloride as by-product which has to be worked up. Finally, alanates or amine-alane adducts ($R_3N$—$AlH_3$) prepared therefrom are reacted with silicon tetrafluoride in organic solvents to form monosilane.

A solvent melt as reaction medium has been used in a continuous or cyclic process and developed for industrial use. In this process, silicon tetrachloride is hydrogenated by means of lithium hydride which is prepared from lithium in an LiCl-KCl melt at 400° C., dissolved in the process and subsequently reacted. Disadvantages are the high temperature, corrosion problems, the high price of lithium compounds and the environmental concerns associated with them, and finally the reprocessing cost for the lithium chloride formed [(1) DE-C 1080077; (2) W. Sundermeyer et al. Angew. Chem 70 (1958) 625].

The direct hydrogenation of silicon tetrachloride in a eutectic mixture of sodium chloride and aluminum chloride (m.p. 108° C.) is described by H. L. Jackson et al. [Inorg. Chem. 2 (1963) 43]. In the reaction of hydrogen with a high molar excess of aluminum powder, 30 g of silicon tetrachloride are hydrogenated at 175° and an industrially impractical pressure of 960 bar in a 400 ml shaking autoclave charged with steel balls for 6 hours to give a conversion of 70–100% and 5.8 g of monosilane. Disilane and dimethylsilane are formed only in very small amounts under analogous reaction conditions because of cleavage of the Si—Si or Si—C bonds. Monosilane is also formed only in traces when the aluminum is not additionally treated with up to 3% of an "activator" such as lithium hydride, lithium alanate, sodium hydride, alkaline earth metal hydrides and the abovementioned melt. The reaction mechanism is said to be the formation of $H_xAlCl_{3-x}$ as hydrogenating agent.

The analogous reaction of (organo)chlorosilanes with hydrogen and aluminum in salt melts comprising sodium chloride and aluminum chloride is described by H. J. Klockner et al. [EP 0412342] as proceeding under atmospheric pressure when the aluminum contains 0.03–0.25% by weight of a hydrogen-transferring metal such as titanium, zirconium, hafnium, vanadium, niobium or nickel, according to the examples as alloy. In addition, this document also claims, inter alia, the same "activators" as those described by H. L. Jackson et al.: Lithium alanate and sodium hydride, and additionally titanium hydride. In another document [DE 4119578.7], lithium hydride (cf. H. L. Jackson et al.) and also zirconium hydride, palladium chloride, nickel chloride and Raney nickel are claimed as "activators". As regards the reaction mechanism, the generation of $H_xAlCl_{3-x}$ as actual hydrogenating compound which is said to be present in a concentration of 0.01–20 mol %, in particular 10 mol %, based on the amount of melt, is once again described. When using a melt having a molar ratio of $NaCl:AlCl_3$=1:1, 90% yields of $SiH_4$ and 83–90% yields of $(CH_3)_2SiH_2$ were observed. However, the conversions (% of the total starting compound used which is reacted) and, even more, the space-time yields (STY; g/l of reaction volume and hour) of the individual components are extraordinarily low. In the case of $SiCl_4$, the conversion is 20% (66 g of 324 g in 6 h) and the STY is only 1.9 g of $SiH_4$/lh. $(CH_3)_2SiH_2$ was able to be obtained in a conversion of only 5–8% (15.5 g of 327 g in 2 h) and an STY of 3–6 g/l h. In each case, only up to about 3% of the hydrogen introduced was reacted, since according to the method described it has to be used in a large, 5–10-fold excess.

It is therefore an object of the invention to develop a process for the direct hydrogenation of Si—Cl bonds using elemental hydrogen at moderate temperatures and pressures, which process avoids the stated disadvantages and makes it possible to prepare silanes in a technically simple and economical manner.

Surprisingly, metals which form interstitial hydrides, preferably titanium, zirconium, vanadium, chromium, manganese, nickel, palladium, platinum and rare earth metals, or combinations thereof, in particular titanium metal, have now been found to be particularly good hydrogen transferrers for achieving this object when they are present in suspension in very finely divided form, preferably when they are produced in situ in a salt melt comprising alkali metal/alkaline earth metal halides and aluminum halide, in particular the chlorides, by reduction of the corresponding metal halide by an electropositive element (halogen acceptor I). As metal halides, it is possible to use all solid or volatile compounds, for example in the case of titanium the compounds of the type $TiX_4$, $TiX_3$, $TiX_2$, or salts containing $TiX_6^{2-}$ or $TiX_6^{3-}$ ions (X=halogen), but preferably $TiCl_4$ or $TiCl_3$, which are dissolved in the melt and reduced to titanium metal by the halogen acceptors I, namely magnesium, calcium or aluminum. The so called "activators" in the form of various previously prepared, expensive hydrides or alloys as are known from the prior art are not necessary in the process of the invention.

The salt melt serving as reaction medium comprises mixtures of alkali metal halides and/or alkaline earth metal halides and aluminum halides, preferably the chlorides. The liquidus curves of the individual systems can be found in standard tables [R. S. Roth, M. A. Clevinger, D. McKenna, Phase Diagrams for Ceramists, National Bureau of Standards, The American Ceramic Society, Inc., Vol. I–V, 1964-83]. The eutectics or melts even richer in $AlCl_3$ can be used, but they suffer from a high degree of $AlC_3$ sublimation, which would require appropriate, technically complicated measures in carrying out the reaction.

| Eutectics: | | |
|---|---|---|
| | $LiAlCl_4$—$AlCl_3$ | m.p. 80° C. |
| | $NaAlCl_4$—$AlCl_3$ | m.p. 113° C. |
| | $KAlCl_4$—$AlCl_3$ | m.p. 133° C. |
| | $Mg(AlCl_4)_2$—$AlCl_3$ | m.p. 184° C. |

It has therefore been found to be advantageous to use the (tetra)chloroaluminates whose vapor pressure becomes significant only far above the reaction temperatures to be employed according to the invention.

Examples are:

| | |
|---|---|
| LiAlCl$_4$ | m.p. 143° C. |
| NaAlCl$_4$ | m.p. 153° C. |
| KAlCl$_4$ | m.p. 256° C. |
| Mg(AlCl$_4$)$_2$ | m.p. 230° C. |
| Ca(AlCl$_4$)$_2$ | m.p. 218° C. |

It has now surprisingly been found that pseudobinary and pseudoternary mixtures of these chloroaluminates are, owing to the favorable change in physical properties of the melt associated therewith, particularly advantageous for the preparation of and the direct hydrogenation using finely dispersed metals forming interstitial hydrides, for example the eutectics:

| | |
|---|---|
| NaAlCl$_4$—KAlCl$_4$ | m.p. 125° C. |
| NaAlCl$_4$—KAlCl$_4$-AlCl$_3$ | m.p. 89° C. |
| NaAlCl$_4$—KAlCl$_4$-MgCl$_2$ | m.p. 125° C. |
| KAlCl$_4$—Ca(AlCl$_4$)$_2$ | m.p. 148° C. |

Preference is given to using the system NaAlCl$_4$—KAlCl$_4$ in a molar ratio of the chloroaluminates of 70:30 (eutectic), advantageously with a further addition of LiAlCl$_4$, e.g. NaAlCl$_4$—KAlCl$_4$—LiAlCl$_4$ in a molar ratio of 70:25:5.

The reactions are carried out at above the melting point of the chloroaluminate system used in the particular case and at below the decomposition temperature of the starting materials to be hydrogenated and of the products, i.e. in the range from room temperature to 600° C., preferably in the range 100–400° C., in particular in the range 150–300° C.

The halogen acceptor I suspended in an at least stoichiometric amount in the chloroaluminate melt by intensive stirring reduces the metal halide added to the metal. The reduction can be carried out under inert gas, but preferably already in a hydrogen atmosphere.

The subsequent hydrogenation of the halogen-substituted silicon compounds in the presence of the metal forming interstitial hydrides is carried out by passing them continuously together with hydrogen into the salt melt with addition of a halogen acceptor II in an at least stoichiometric amount based on the chlorosilane used. For further hydrogenations in the same melt, it is only necessary to add further halogen acceptor II in an amount corresponding to that which has been consumed. An advantage which has been found is that the same electropositive elements can be used as halogen acceptors I and II with the choice of electropositive elements depending on the melt system used in each case.

As regards the particle size of the added halogen acceptors I and II, there is no need to use fine powder grades which are particularly difficult to produce and handle. Even if these can be used in principle in the reaction according to the invention, preference is given to powders of, for example, ordinary smelter aluminum having a particle size range of 150–1000 μm. Even larger particle sizes are likewise suitable, as long as they do not have an adverse effect on the stirrers of the reactor.

The hydrogenation is normally carried out at atmospheric pressure. It can also be carried out at superatmospheric pressures to increase the hydrogen solubility, although a similar effect can also be achieved by dispersion by means of suitable, preferably sparging, stirrer types. These offer the additional advantage that always only the hydrogen consumed has to be replaced in a stoichiometric amount, based on the halosilane to be hydrogenated, while the passage of a large excess of hydrogen, which can in principle also be employed in the process of the invention, is disadvantageous in terms of its recovery or entrainment of product. The silanes are usually separated off by condensation in cold traps and are subsequently purified by low-temperature rectification [H. Hiller, gas aktuell (Messer Griesheim), 33, 1987, 2–6]. At high throughputs of the hydrogen/halosilane mixture, partially hydrogenated (organo)chlorosilanes were also able to be obtained as by-products using the process of the invention.

The addition of an excess of dissolved and/or suspended alkali metal halide or alkaline earth metal halide (chloride) has been found to have a particularly good promoting effect on the reaction in the hydrogenation of the invention; this additional halide is preferably used in such a mixing ratio that the liquidity of the salt melt is not significantly changed, if at all. The continual increase in the volume of the melt caused by the reaction by-products is countered by occasionally draining or siphoning off part of the melt and working it up separately. The use of a salt melt as reaction medium also. makes it possible, as a combination step, to recover the halogen acceptor metals by electrolysis directly in the salt melt using methods known from the literature [H.J. Klockner et al., Z. anorg. allg. Chem. 509 (1984) 76–84], advantageously also using a self-dissolving silicon anode and with simultaneous production of silicon tetrachloride [W. Sundermeyer et al., Chem. Ing. Techn. 37, (1965) 14].

The following examples demonstrate that silanes can be produced in high yields and at conversions and space-time yields far superior to the prior art by means of the process of the invention.

Examples

Example 1

4 mol (533.36 g) of AlCl$_3$ were mixed with 2.8 mol (163.64 g) of dry NaCl and 1.2 mol (89.64 g) of dry KCl and melted at 200° C., for example in a reaction vessel described in the literature [G. Brauer, Handbuch der präparativen anorganischen Chemie, 3rd edition, vol. 1, p. 101, F. Enke Verlag, Stuttgart 1975]. The desired reaction temperature (see Table 1) was subsequently set and in each case 0.1 mol of halide of the appropriate metal forming interstitial hydrides was dissolved or suspended in the melt and reduced to the metal in a hydrogen atmosphere using 0.2 mol of Mg or Ca or 0.15 mol of Al as halogen acceptor I.

Subsequently, after addition of 0.2 mol of the halogen acceptor II, in each case 0.08 mol (10 ml) of (CH$_3$)$_3$SiCl in a stream of hydrogen (1 standard l/h) was passed through over a period of 1.5 h. The product mixture of (CH$_3$)$_3$SiCl and (CH$_3$)$_3$SiH was collected in two cold traps (−78° C./−196° C.) and analyzed by gas chromatography.

For comparison, the aluminum powder alloyed with 0.2% by weight of titanium corresponding to the prior art was reacted with the H$_2$/(CH$_3$)$_3$SiCl mixture under analogous reaction conditions (cf. first line of Table 1).

TABLE 1

(for Example 1)

NaAlCl$_4$—KAlCl$_4$ melt

| Halide | Metal | Halogen acceptor I | Halogen acceptor II | Conversion in % | | | | |
|---|---|---|---|---|---|---|---|---|
| | | | | 200° C. | 230° C. | 250° C. | 280° C. | 300° C. |
| TiCl$_4$ | Ti | Mg | Al alloy (0.2% of Ti) | 3.5 | 2.7 | 4.7 | | |
| TiCl$_4$ | Ti | Ca | Mg | 1.0 | | 3.1 | 4.8 | 2.9 |
| TiCl$_4$ | Ti | Al | Al | | >95 | | | |
| ZrCl$_4$ | Zr | Al | Al | >95 | >95 | >95 | | |
| VCl$_3$ | V | Mg | Al | 9.2 | 18.8 | 10.7 | | |
| VCl$_3$ | V | Al | Mg | 12.3 | | 12.3 | 31.0 | |
| CrCl$_3$ | Cr | Mg | Al | 11.4 | 64.1 | 54.6 | | |
| CrCl$_3$ | Cr | Al | Mg | 31.0 | | 43.2 | 24.2 | |
| MnCl$_2$ | Mn | Mg | Al | 5.0 | 9.2 | 18.8 | | |
| MnCl$_2$ | Mn | Al | Mg | 27.5 | | 53.9 | 55.9 | 56.9 |
| NiCl$_2$ | Ni | Ca | Al | 13.6 | 29.8 | 35.6 | | |
| NiCl$_2$ | Ni | Mg | Al | | 11.2 | | | |
| NiCl$_2$ | Ni | Al | Mg | 3.9 | | 25.4 | 43.2 | 32.0 |
| PdCl$_2$ | Pd | Ca | Al | 1.0 | 4.6 | 7.1 | | |
| PdCl$_2$ | Pd | Al | Al | 10.8 | 21.4 | | | |
| K$_2$PtCl$_6$ | Pt | Ca | Al | 7.1 | 12.1 | 14.7 | | |
| K$_2$PtCl$_6$ | Pt | Al | Al | | 19.2 | | | |
| LnCl$_3$ | Ln | Ca | Al | 20.9 | 24.3 | 32.6 | | |
| LnCl$_3$ | Ln | Mg | Al | | 11.0 | | | |
| LnCl$_3$ | Ln | Mg | Mg | 13.9 | | 16.1 | | |
| FeCl$_3$ | Fe | Mg | Mg | 13.8 | | 10.0 | 47.6 | 26.5 |
| CoCl$_2$ | Co | Mg | Mg | 9.9 | | 19.4 | 21.9 | |
| AgCl | Ag | Al | Al | 8.8 | 27.5 | 27.4 | | |

Example 2

In the reaction vessel described, a mixture of 393 g of dry NaCl, 215 g of dry KCl and 1067 g of AlCl$_3$ was melted at about 150° C. After setting the temperature to about 300° C., 190 g of TiCl$_4$ were introduced in an H$_2$ atmosphere and in the presence of 180 g of Al powder over a period of 2 h while stirring and reduced to titanium metal.

After adjusting the reaction temperature to 205° C. and adding 20 g of Al powder, 171 g of (CH$_3$)$_3$SiCl in a hydrogen stream of 12 l/h were passed into the titanium metal suspension with vigorous stirring over a period of 2 h.

15.9 g of (CH$_3$)$_3$SiCl were recovered and 148.6 g of (CH$_3$)$_3$SiCl were reacted, which corresponds to a conversion of 87%. The yield of (CH$_3$)$_3$SiH was 90.5 g (corresponding to 89%) and the STY was 45 g/lh.

Example 3

35 g of Al powder were added to the same melt from Example 2, and 208.5 g of (CH$_3$)$_2$SiCl$_2$ were introduced at 210° C. together with a hydrogen stream of 18 l/h over a period of 2.5 h.

After recovery of 72.6 g of (CH$_3$)$_2$SiCl$_2$ by rectification (conversion: 65%), 60 g of (CH$_3$)$_2$SiH$_2$ were obtained, corresponding to a yield of 94.5% and an STY of 24 g/lh.

Example 4

35 g of Al powder were added to a melt prepared as described in Example 2, and 150 g of SiCl$_4$ were introduced at 230° C. in a hydrogen stream (50 l/h) over a period of 1 h.

54 g of SiCl$_4$ were recovered, which corresponds to a conversion of 64%. 16.7 g of monosilane SiH$_4$ were isolated, corresponding to a yield of 92% and an STY of 16.7 g/l h.

Example 5

35 g of Al powder, 65 g of NaCl and 20 g of LiCl were added to the same melt from Example 4, and 136 g of SiHCl$_3$ were then introduced together with 40 l/h of hydrogen over a period of 1 h.

After 14 g of SiHCl$_3$ had been separated off (conversion: 89.7%) by rectification, 27.6 g of SiH$_4$ were isolated, which corresponds to a yield of 96% and an STY of 27.6 g/lh.

Example 6

10 g of Al powder were added to a melt prepared as described in. Example 2, and 26.9 g of Si$_2$Cl$_6$ were introduced at 230° C. together with a hydrogen stream of 5 l/h over a period of 2.5 h.

After recovery of 5.4 g of Si$_2$Cl$_6$ by rectification (conversion: 80%), 3 g of Si$_2$H$_6$ corresponding to a yield of 60% and 2.05 g of SiH$_4$ corresponding to a yield of 40% were obtained.

What is claimed is:

1. A process for the hydrogenation of halogen-substituted silicon compounds, comprising:
    reacting said halogen-substituted silicon compounds with hydrogen in a chloroaluminate salt melt as a reaction medium containing a finely divided metal capable of forming interstitial hydrides which are suspended in the melt, the finely divided interstitial metal hydrides being formed in situ in the melt by reduction of a metal halide with an electropositive element as a halogen acceptor I selected from the group consisting of magnesium, calcium and aluminum.

2. The process as claimed in claim 1, wherein the metal of the interstitial metal hydrides is titanium, zirconium, vanadium, chromium, manganese, nickel, palladium, platinum, a rare earth metal or a combination thereof.

3. The process as claimed in claim 2, wherein said metal is titanium.

4. The process as claimed in claim 1, which further comprises adding additional halogen-substituted silicon compound to the chloroaluminate salt melt with additional halogen acceptor as halogen acceptor II, wherein the amount of additional halogen acceptor II added corresponds stoichiometrically to the amount of halogen-substituted silicon compound added.

5. The process as claimed in claim 1, wherein the chloroaluminate salt melt further comprises an alkali metal halide and/or alkaline earth metal halide.

6. The process as claimed in claim 1, wherein the reaction is conducted at a temperature above the melting point of the chloroaluminate salt melt and below the decomposition temperature of the silicon-hydrogen compound.

7. The process as claimed in claim 6, wherein the reaction is conducted in the range from room temperature to 600° C.

8. The process as claimed in claim 1, wherein the halogen-substituted silicon compound which is reacted with hydrogen is trichlorosilane ($SiHCl_3$), tetrachlorosilane ($SiCl_4$) or hexachlorodisilane ($Si_2Cl_6$).

9. The process as claimed in claim 1, wherein the halogen-substituted silicon compound is an organohalosilane.

10. The process as claimed in claim 9, wherein the organohalosilane is methyltrichlorosilane, dimethyldichlorosilane or trimethylchlorosilane.

11. The process as claimed in claim 1, wherein the chloroaluminate salt melt is electrolyzed thereby enabling recovery of acceptor metal in the melt.

12. The process as claimed in claim 11, which is conducted in an electrochemical cell containing a silicon anode immersed in the electrolysis medium containing a melt of chloroaluminate.

13. The process as claimed in claim 7, wherein said temperature ranges from 100–400° C.

14. The process as claimed in claim 13, wherein said temperature ranges from 150–300° C.

15. The process as claimed in claim 4, wherein the halogen acceptors I and II are particulate and have a powder size range of 150–1,000 $\mu$m.

16. The process as claimed in claim 1, wherein the hydrogenation reaction is conducted under superatmospheric pressure.

* * * * *